United States Patent [19]

Searle

[11] Patent Number: 5,341,683
[45] Date of Patent: Aug. 30, 1994

[54] DYNAMIC RAIL LONGITUDINAL STRESS MEASURING SYSTEM

[76] Inventor: Donald S. Searle, 206 Main St., Hartville, Wyo. 82215

[21] Appl. No.: 892,183

[22] Filed: Jun. 2, 1992

[51] Int. Cl.$^5$ .................. G01N 29/18; G01N 29/24
[52] U.S. Cl. ........................... 73/597; 73/610; 73/624; 73/636; 73/639
[58] Field of Search .............. 73/597, 598, 602, 609, 73/610, 619, 633, 635, 636, 639, 624

[56] References Cited

U.S. PATENT DOCUMENTS

| | | | |
|---|---|---|---|
| 3,364,732 | 1/1968 | Sasaki | 73/597 |
| 3,442,119 | 5/1969 | Cowan | 73/639 |
| 3,937,068 | 2/1976 | Joy | 73/636 |
| 3,962,908 | 6/1976 | Joy | 73/636 |
| 4,004,455 | 1/1977 | McKee et al. | 73/615 |
| 4,044,594 | 8/1977 | Owens et al. | 73/621 |
| 4,165,648 | 8/1979 | Pagano | 73/625 |
| 4,167,879 | 9/1979 | Pedersen | 73/610 |
| 4,174,636 | 11/1979 | Pagano | 73/636 |
| 4,235,112 | 11/1980 | Kaiser | 73/634 |
| 4,429,576 | 2/1984 | Norris | 73/636 |
| 4,457,178 | 7/1984 | Turbe et al. | 73/636 |
| 4,468,966 | 9/1984 | Bradshaw | 73/636 |
| 4,662,224 | 5/1987 | Turbe | 73/636 |
| 4,689,995 | 9/1987 | Turbe | 73/636 |
| 4,700,574 | 10/1987 | Turbe | 73/636 |
| 4,932,618 | 6/1990 | Davenport et al. | 246/122 R |
| 5,020,371 | 6/1991 | Panetti | 73/636 |

OTHER PUBLICATIONS

"Measurement of Applied and Residual Stresses Using an Ultrasonic Instrumentation System" by B. E. Gordon, Jr. (ISA Transactions–vol. 19, No. 2) (1980) pp. 33–40.

Primary Examiner—Hezron E. Williams
Assistant Examiner—Rose M. Finley

[57] ABSTRACT

A system and method for dynamically and non-destructively measuring the longitudinal stresses in a rail of a continuous rail track includes an ultrasonic transmitter which transmits coded focused shear pulses through a rail which are subsequently received by a linear array of sensors. A displacer adjusts the separation between the transmitter and the sensors to maximize the signal intensity received by a centrally located one of the sensors. A data processor, in conjunction with a rail height detector, a rail temperature detector, and a rail splice detector, dynamically determines the longitudinal stresses in the rail as a function of the velocity of propagation of the pulses, the stress free temperature (SFT) of the rail, and activates a rail marker to mark portions of the rail having unacceptable longitudinal stresses. Stress and related data is recorded on a data log. A video camera provides observed rail separation data to the data processor. A modified embodiment alters the angle of incidence of the transmitted pulses to adjust for changes in velocity of propagation caused by changes in longitudinal stress.

21 Claims, 2 Drawing Sheets

Fig.1.

DYNAMIC RAIL LONGITUDINAL STRESS MEASURING SYSTEM

BACKGROUND OF THE INVENTION

1. Field of the Invention

The present invention relates to an apparatus and method for measuring the stress in an elongated steel member and, specifically, without limitation, for dynamically measuring the longitudinal stress in each rail of a railroad track having continuous rails.

2. Description of the Related Art

In the past, railroad tracks have largely been constructed by anchoring discrete rail sections having finite length to an underlying road bed in an end-to-end relationship. A distinct advantage provided by such an arrangement is that differences in thermal coefficient of expansion between the metal rail sections and the road bed is absorbed by mechanical joints or gaps, which are purposefully provided between adjacently spaced sections as the rail sections are installed. Unfortunately, those gaps cause substantial maintenance problems, which generally requires lifting and aligning selected ones of the rail sections, reconstruction of the sub-grade or road bed, and the like. Besides added maintenance problems, the mechanical joints also cause ride, noise and comfort problems.

During the last three decades, an effort has been underway to eliminate the mechanical joints in railroad tracks. That effort has largely involved constructing tracks having continuous rails by welding or otherwise joining together the ends of the adjacently spaced rail sections, forming a structure sometimes referred to as continuous rail track, or "CR" track. The technology associated with the construction of a CR track is well known in the prior art.

The elimination of mechanical joints from rail tracks by joining together the rail section ends, however, creates new problems arising from seasonal variations in the ambient temperature. In tropical climates, the ranges between the temperature extremes are generally moderate, which does not pose a substantial problem for rail systems. In temperate climates, however, such as those in the United States, Japan and Europe, the ranges of temperature extremes are sufficient to cause catastrophic, temperature induced failures in rail systems, including both rail pull-apart and rail-buckle failures, as hereinafter described.

For example, an unanchored 100-mile length of continuous rail in certain areas of a temperate climate could experience a change in length of over 700 feet from one seasonal temperature extreme to the other. By anchoring the rail to railroad ties, changes in the overall length of the rail can be largely prevented but, instead, resultant localized longitudinal stresses are created internally in the rail.

As the rails of a CR track are initially installed and anchored to a road bed, each of the rails has zero longitudinal stresses. The temperature at which the CR track is installed is sometimes referred to as the stress-free temperature, or "SFT".

As the ambient temperature falls below the SFT, tensile longitudinal stresses are created internally in each rail of the CR track due to the greater thermal coefficient of expansion of the metal rails relative to that of the underlying road bed. If the difference between the reduced ambient temperature and the SFT is extreme, the tensile stresses in the rails can potentially attain sufficient magnitude to actually cause one or both of the rails to pull apart.

Preferably, a CR track is installed at temperature such that the magnitude of the maximum, cold-temperature induced, tensile stresses are substantially less than those required to produce a rail pull-apart. If one or both of the rails of a CR track should pull apart in extremely cold conditions, risk exposure for derailment is generally minimal as pull-apart failure usually occurs beneath a moving train and the resulting separation between the two ends at the pull apart may not be sufficient to cause derailment. Failure to anchor the track at an appropriate SFT, however, may result in much larger separations—gaps of up to 6 inches have been recorded—which do pose a serious threat of derailment.

Fortunately, pull-apart failure can easily be detected by establishing an electrical track circuit using the rails as part of the conduction path, which becomes "open" if one of the rails of the CR track pulls apart.

Similarly, as the ambient temperature climbs above the SFT, compressive stresses are created internally in each of the rails of the CR track. If the difference between the elevated ambient temperature and the SFT is extreme, the compressive stresses in the rails can potentially attain sufficient magnitude to actually cause one or both of the rails to buckle. Theoretical calculations indicate that a stress of approximately 200 Kips (kilopounds) is sufficient to cause rail buckle during extreme Summer temperatures. (Strictly speaking, stress is a measure of force per unit area; however, since the cross-sectional area of a given rail is substantially constant, the expression herein of longitudinal rail stress in force units should be interpreted to mean force per cross-sectional area of the rail.)

Such buckling, which is random, unpredictable and a major source of derailments, generally occurs as a result of the CR track being anchored at a temperature whereby excessive compressive stresses are generated in the rails during peak Summer temperatures. The ability of a train to negotiate a lateral displacement, which is typical of rail-buckle, is minimal. As a result, rail-buckle poses a substantially greater risk of derailment than does a rail pull-apart since the former cannot be detected by a conventional track circuit.

To reduce the risk of failures occurring during both upper and lower temperature extremes, the rails of a CR track are generally anchored to the underlying road bed at a preferred SFT, or "PSFT", which is generally situated approximately mid-way between the upper and lower extreme temperatures normally realized for each locality containing the rails. The PSFT is generally defined as the CR installation temperature at which the CR track, hopefully, will not fail due to rail pull-aparts during extremely cold ambient temperatures, nor fail due to rail-buckle during extremely hot ambient temperatures.

The PSFT for any particular locality should take into account several variables, including temperature extremes, rail size and cross-section, track structure design, curves and tangent lengths, rail anchor design, tie type and weight, number of anchors per tie, track geometry and profile, ballast modulus, etc. If anchoring of the continuous rails occurs at temperatures substantially removed from the PSFT for a particular locality, the risk that the track may fail either from rail pull-apart or from rail-buckle is substantially enhanced.

For example, in one locality in Wyoming, the rails of a CR track are generally constructed of 136 lb./yd. rail stock and are generally anchored at a PSFT of approximately 95° F. (In a 136-lb./yd. rail, the longitudinal stresses change by approximately 1.8 Kips/° F.) There, rail temperature extremes ranging from −50° F. to 160° F. have been recorded. Therefore, rail-buckle can occur if a CR track is anchored at temperatures substantially below the PSFT of 95° F.

In one instance during extreme Winter conditions, a rail of a CR track pulled apart with the width of the resulting gap between the two rail segments indicating that a stress of approximately 300 tons/inch had caused the failure. If the rail had been properly installed at the PSFT of 95° F., then an ambient temperature of −50° F., or temperature differential of 145° F. from the PSFT, would have been insufficient to develop the indicated catastrophic tensile stress.

Even if a CR track is anchored at the PSFT, the desired stress characteristics arising therefrom is compromised each time a railroad maintenance crew routinely repairs fatigue defects in the track, which has a frequency of occurrence in North America alone of approximately 200,000 annually. The inability to reestablish the PSFT characteristics at each site after such repair results in previously unascertainable, cumulative deviations of the actual longitudinal rail stresses of the repaired rail from those which preferably would exist relevant to the PSFT. Destruction of the preferred internal stressing characteristics is accentuated for repairs which are performed during extreme temperature conditions.

For example, the installation of a rail insert, sometimes referred to as a "plug", in extremely cold ambient temperatures far below the PSFT can result in not only relieving the existing tensile stresses which would otherwise have countered a certain portion of the compressive stresses anticipated to arise during the hot Summer season.

Similarly, the opposite effect is realized if a stress-free plug is inserted in extremely hot ambient temperature, far above the PSFT, which then substantially aggravates the excessive, relatively localized tensile stresses occurring during the cold Winter season.

The seasonality of the longitudinal stresses, complicated by the continuity interruptions, resulting from maintenance and repair of rail fatigue and other defects, is believed to cause the existing longitudinal rail stresses to be largely unknown, thereby making predictability of rail-buckle failures virtually impossible.

Even if the rails of a CR track are installed at or near the PSFT, each of the rails and the road bed are dynamic systems. Thus, absolute longitudinal stresses in the rails need to be periodically monitored and controlled.

The economic consequences of derailments is substantial. In 1989, the FRA reported that within the United States alone, rail induced derailments caused damages of approximately $56,000,000. Although not all of those derailments arose from a single type of cause, rail-buckles were responsible for a significant portion of those damages, not to mention the concurrent loss of life.

Although various methods and apparatus have been developed in an attempt to prevent rail-buckle in a CR track, none of them are capable of dynamically, accurately, and non-destructively measuring the absolute longitudinal stress in the rails of a CR track. For example, traditional methods for determining longitudinal stresses in a rail of a CR track includes severing the rail, observing the resultant gap or closure between the severed ends, and analyzing the width of the gap or closure as a function of the ambient temperature. Obviously, this method is a destructive and undesirable procedure.

Fortunately, the propagation velocity of ultrasound through a continuous rail varies as a function of the magnitude of the internal stresses of the rail. Unfortunately, however, other methods and apparatus utilizing ultrasonic techniques for detecting various types of flaws and defects in rails have suffered from interference arising from flange noise. Flange noise is generated as the flanges of the wheels of a deployable vehicle containing the apparatus roll along the rails such that multi-point contact is made between the rails and the wheels at different rolling diameters, thereby causing a situation sometimes referred to as "slip".

The sound spectrum generated by slip generally spans a particular ultrasonic frequency, such as 2.25 MHz., which could be usefully employed to measure longitudinal stresses. Without filtering or otherwise minimizing the effects of the flange noise, the randomness and magnitude of this interference is sufficient to mask the useful data which could otherwise be obtained by ultrasonic techniques.

What is needed in an apparatus and a method, which can be used to minimize or eliminate the effects of sonic interference from flange noise and which, therefore, can be used to dynamically and non-destructively measure the absolute longitudinal stresses in the rails of a CR track.

SUMMARY OF THE INVENTION

An improved rail stress measuring system is provided for dynamically and non-destructively measuring the longitudinal stresses in a rail of a continuous rail track. The system includes an apparatus having an ultrasonic transmitter which transmits coded, focused shear wave pulses which are refracted longitudinally through a rail. The transmitted pulses are subsequently received by a plurality of sensors which are arranged in an array aligned with the axis of the rail. A focuser collimates the transmitted pulses and focusses them on the array. The outputs of each of the sensors is filtered by one of a plurality of filters which are tuned to the coded pulses, thereby eliminating interference from other extraneous sources of ultrasonic waves, such as those arising from rail squeal.

A displacer adjusts the separation between the transmitter and the sensors to maximize the signal intensity received by a centrally located one of the sensors relative to the signal intensities received by other ones of the sensors situated on either side of the centrally located sensor. The displacer also adjusts the equilibrium configuration, as the angle of refraction changes due to changes in the velocity of propagation of the pulses through the rail which varies as a function of the longitudinal stresses in the rail. A displacement encoder communicates the changes in the separation between the transmitter and the sensors to a data processor.

A rail height detector comprising an transmitter/receiver arrangement is adapted to dynamically determine the height of the rail by measuring the transit time of an ultrasonic signal transmitted perpendicularly through the rail.

A rail temperature detector is adapted to dynamically and remotely determine the temperature of the rail by infrared techniques.

A rail splice detector comprising a transmitter/receiver arrangement is adapted to dynamically determine the boundaries between individual rail sections of the continuous rail by detecting the splines generally used to connect the rail sections in an end-to-end configuration. The rail splice detector alerts the data processor of the boundary to prevent the displacer from unsuccessfully seeking the equilibrium configuration.

A site identifier identifies the site at which each of the pulses was transmitted through the rail, which information is communicated to the data processor.

The data processor, which determines the longitudinal stresses in the rail as a function of the velocity of propagation of the pulses, calculates the stress free temperature (SFT) of the rail and compares the SFT with the preferred SFT for the locality of each of the pulse sites. For those portions of the rail having longitudinal stresses beyond acceptable limits, the data processor activates a rail marker, which appropriately marks the rail with coded data providing the corrective measures needed to adjust the SFT to within acceptable limits.

Stress and related data is recorded on a data log for selected ones of the pulse sites. A video camera provides observed rail separation data to the data processor for comparison with desired rail separation.

A modified embodiment of a rail stress measuring system is adapted to alter the angle of incidence of the transmitted pulses to adjust for changes in velocity of propagation through the rail caused by changes in longitudinal stress.

The system includes a method for dynamically and non-destructively measuring the longitudinal stresses in a rail of a continuous rail track as a function of changes in the angle of refraction of an ultrasonic shear wave transmitted through the rail.

The system also includes a method for dynamically and non-destructively measuring the longitudinal stresses in a rail of a continuous rail track as a function of changes in the angle of incidence of an ultrasonic shear wave transmitted through the rail.

PRINCIPAL OBJECTS AND ADVANTAGES OF THE INVENTION

Therefore, the principal objects and advantages of the present invention include: providing an apparatus and method for measuring the absolute longitudinal stresses in a rail of a continuous rail track; providing such an apparatus and method for dynamically measuring the absolute longitudinal stresses in a rail of a continuous rail track; providing such an apparatus and method for ultrasonically measuring the longitudinal stresses in a rail of a continuous rail track; providing such an apparatus and method which determines changes in the longitudinal stress in a rail of a continuous rail track from changes in the angle of refraction of an ultrasonic pulse transmitted into the rail; providing such an apparatus and method which determines changes in the longitudinal stress in a rail of a continuous rail track from changes in the angle of incidence required to maintain the triangulation of an ultrasonic pulse transmitted through the rail; providing such an apparatus and method which minimizes or eliminates the effects of flange noise interference; providing such an apparatus and method which non-destructively measures the absolute longitudinal rail stress in a rail of a continuous rail track; providing such an apparatus and method which prescribes moderate-ambient-temperature corrective repairs for minimizing or eliminating rail failures at extreme ambient temperature conditions by conducting ultrasonic measurements at ambient temperatures; providing such an apparatus and method for measuring both compressive and tensile longitudinal stresses in rails of a continuous rail track; providing such an apparatus and method which can be easily adapted to field measurement; providing such an apparatus and method which can be easily deployed on a deployable vehicle; providing such an apparatus and method which can be utilized to measure longitudinal rail stresses in different types of track, such as track with either wood or concrete ties, tangent track, curved track, and the like; providing such an apparatus and method for enabling a user to predict the anticipated extreme longitudinal stresses in a rail at the temperature extremes expected for a particular locality based on measurements taken in that locality at a moderate ambient temperature; providing such an apparatus and method which can be used in conjunction with routine rail maintenance repairs without creating unwanted stress characteristics in the rail; and generally providing such an apparatus and method with is reliable and efficient, provides long-life, requires minimal maintenance, and generally provides the benefits for its intended purposes.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally refers to a dynamic rail longitudinal stress measuring system in accordance with the present invention, as shown in FIGS. 1 through 7. It is to be understood that many of the applications of the system 1 involves the measurement of longitudinal stress in each rail of a two-rail track. In that case, such applications generally would utilize two of the systems 1, one for each of the rails of the track. To simplify the following discussion, however, the system 1 as applicable for a single rail will be described.

The system 1 generally includes transmitting means 3 for transmitting an ultrasonic pulse 5 generally longitudinally through a rail 7, receiving means 9 for receiving the transmitted ultrasonic pulse 5, and analyzing means 11 for analyzing the longitudinal stress in the rail 7 as a function of the velocity of propagation of the pulse 5 through the rail 7, as hereinafter described.

The transmitting means 3 generally includes a first or longitudinal transmitter 13, such as Model No. AEG100 as provided by Posstech, Inc., Guernsey, Wyo., or the like, which transmits ultrasonic pulses longitudinally through the rail 7. A coder 15, such as Model No. POST1 as provided by Posstech, Inc., or the like, is adapted to impress a coded configuration or signature upon the pulse 5 transmitted by the longitudinal transmitter 13. Triggering means 16, such as a shaft encoder, Part No. 924-01002-5721 as provided by BEI Motion Systems, or the like, is adapted to trigger the transmitter 13 to periodically transmit the coded pulse 5 at selected intervals along the rail 7, such as every 10 mm. or other suitable time or distance interval.

Figures 2, 4, 5:
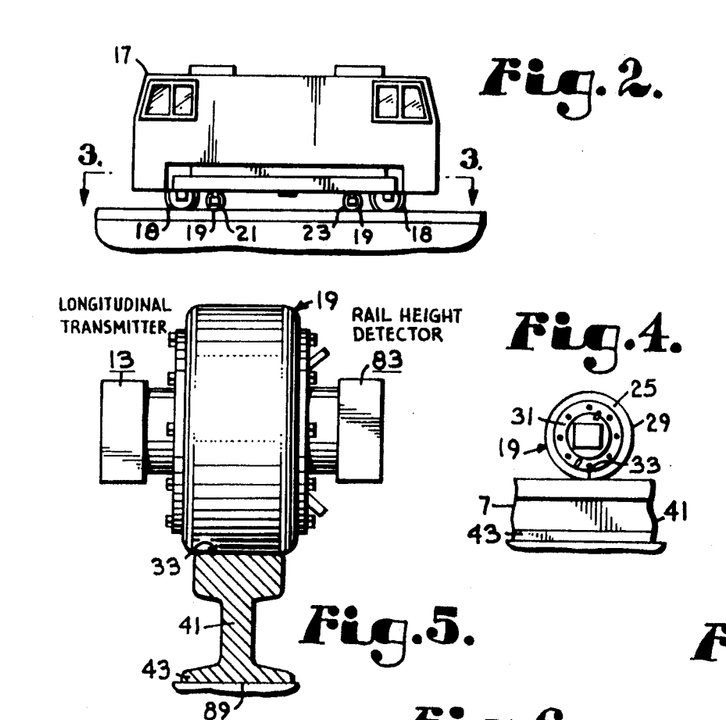
FIG. 2 is a side elevational view at a reduced scale of a rail deployable vehicle on which the rail stress measuring system of the present invention is carried during operation.
FIG. 4 is a fragmentary side elevational view of a test wheel of the rail deployable vehicle of the system.
FIG. 5 is a greatly enlarged transverse sectional view of the test wheel illustrated in FIG. 4.

The system 1 is mounted on a deployable vehicle 17 having two mated pairs of flanged wheels 18 and two mated pairs of test wheels 19, each pair having first and second roller units 21 and 23. Each of the test wheels 19 has a peripheral portion 25 constructed of neoprene plastic or other suitable membrane-like, flexible material, which forms a cavity 27 within the respective test wheel 19. Each of the cavities 27 contains a fluid 29.

A transducer in communication with the transmitter 13, which transmits the pulse 5, is mounted such that the pulse 5 is directed into the rail 7 at a first interface 33 between the rail 7 and the peripheral portion 25 of the first roller unit 21 of the vehicle 17 such that the pulse 5 propagates through the rail 7. The transmitter 13 is oriented such that the pulse 5 is directed at a selected angle of incidence 35 (FIG. 6), which generates a refracted pulse 37 having an angle of refraction 39, whereby the refracted pulse 37 is a shear wave. In one application of the present invention, the angle of refraction 39 used to provide a shear wave in the rail 7 was approximately 70°. The transmitter 13 is directed such that the refracted pulse 37 propagates through a web 41 of the rail 7 towards a base 43 of the rail 7 whereat the pulse 37 is internally reflected in the rail 7.

Preferably, the fluid 25 contained in the cavities 27 generally comprises an anti-freeze-type material, such as a suitable mixture of water and ethylene glycol, calcium chloride, or the like. The composition of the fluid 25 is selected to provide a relatively constant velocity of propagation of the pulse 5 therethrough even though the temperature of the fluid 25 may vary.

For example, the fluid 25 may have three parts of water to two parts of ethylene glycol and be maintained at approximately 85° F. Under those conditions, the velocity of propagation of ultrasonic waves therethrough is 1,608 meters/second, which is relatively constant over a temperature variation of approximately ±50° F.

Figure 1:
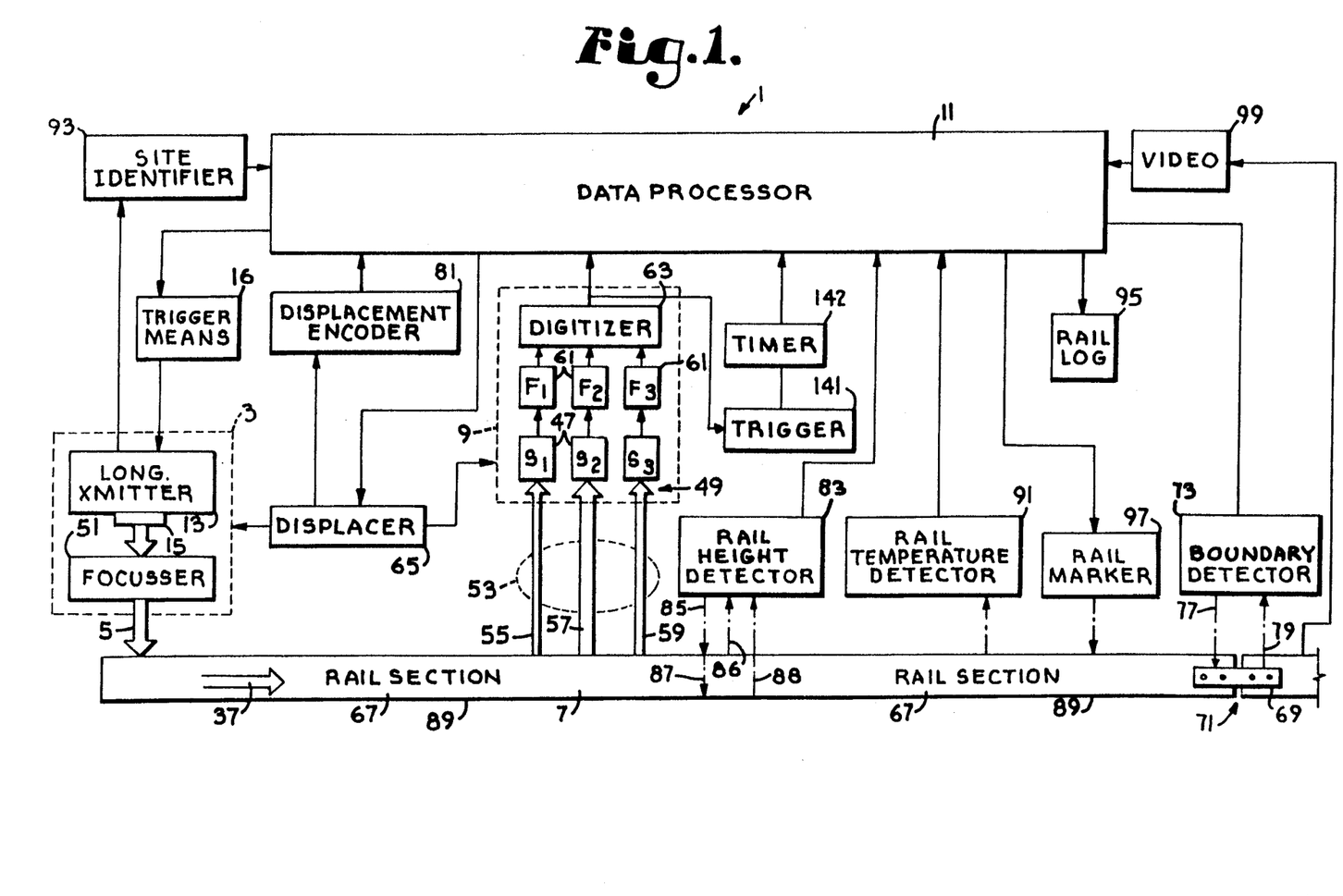
FIG. 1 is a block diagram illustrating the principal functional components of a dynamic rail longitudinal stress measuring system embodying the present invention.

The receiving means 9 (FIG. 1) generally includes a plurality of receiver transducers or sensors 47 spaced in a linear array 49, which is aligned with the axis of the rail 7. FIG. 1 illustrates one of the arrays 49 having three of the sensors 47—designated "$S_1$", "$S_2$", and "$S_3$". It is to be understood that the array 49 may have any number of the sensors 47.

In one example, the array 49 had eight of the sensors 47 and three of those sensors 47, equidistantly spaced, were selected for use of the system 1. It is foreseen that for applications requiring fewer than all of the sensors 47 in the array 49, the selected sensors 47 may be adjacently spaced or include other non-used sensors 47 spaced therebetween. The sensors 47 are generally spaced such that the reduction of signal amplitude varies by approximately 0.5 db between adjacently spaced ones of the sensors 47.

The system 1 generally includes beam focusing means or focuser 51, such as a lens constructed of lucite or other suitable material or lens configuration, adapted to appropriately focus and collimate the pulse 5 such that the refracted pulse 37 forms an emitted pulse 53 which is refracted and emitted from the rail 7. The pulse 5 is focused such that divergence of the pulse 5, prior to reception of the emitted pulse 53 by the receiving means 9, is minimized. For example, the pulse 5 is focused whereby the image thereof is slightly converging at the receiving means 9, with the image having a diameter of approximately 10 mm.

The emitted pulse 53 is shown as having three components in FIG. 1, designated by the numerals 55, 57, and 59, respectively. It is to be understood, however, that the intensity or signal amplitude of the pulse 5 is greatest along the axis of the pulse 5, which is intended for the sensor $S_2$ and which is diagrammatically represented by the pulse component 57 in FIG. 1, with the off-center intensity of the pulse 5 at the receiving means 9 dropping off rapidly to each side of the axis of the pulse 5, which is intended for the sensors $S_1$ and $S_3$ and which is diagrammatically represented by the pulse components 55 and 59 in FIG. 1.

The receiving means 9 also generally includes noise avoidance means, such as a plurality of electronic filters 61, one for each of the sensors 47, designated "$F_1$", "$F_2$", and "$F_3$" in FIG. 1. Each of the filters 61 is designed to recognize the signature impressed on the pulse 5 by the transmitter 13, such that the emitted pulse 53 can be readily separated electronically from undesired ambient and flange noise interference signals received by the sensors 47.

The system 1 may also include auxiliary filtering means (not shown), which are adapted to filter extraneous corruptions of the pulse train arising from interferences caused by chemical and metallurgical influences arising from material variations and rail length variations of the individual sections used to construct the rail 7. For example, the auxiliary filtering means may include computer software contained by the data processor 11, which is designed by methods commonly known in the art, to remove such influences from data contained in the emitted pulse 53.

Outputs from the filters $F_1$, $F_2$ and $F_3$ are fed into a digitizer 63, which converts the signal amplitude respectively received by the sensors $S_1$, $S_2$ and $S_3$ to digital data which the data processor 11 analyzes. A displacer mechanism 65, such as a servomechanism in combination with a hydraulically activated linear motor or other suitable arrangement commonly known in the art, is adapted to increase or decrease the displacement between the transmitting means 3 and the receiving means 9, as controlled by the processor 11, whereby maximum signal intensity of the pulse 53 is received by the sensor $S_2$ and lesser, approximately equal, signal intensities are received by the sensors $S_1$ and $S_3$.

For those instances where the signal intensity received by the sensor $S_2$ is not greater than the signal intensities received by each of the sensors $S_1$ and $S_3$, or the signal intensity received by one of the sensors $S_1$ and $S_3$ is greater than that received by the other one of the sensors $S_1$ and $S_3$, the data processor 11 will activate the displacer 65 such that the distance between the transmitting means 3 and the receiving means 9 is increased or decreased, as logically appropriate, whereby the signal intensity received by the sensor $S_2$ is greater than the signal intensities received by each of the sensors $S_1$ and $S_3$ and the signal intensities received by each of the sensors $S_1$ and $S_3$ are substantially equal, a configuration sometimes referred to herein as an "equilibrium" configuration.

As the rail 7 of a continuous track is formed, rail sections 67 are aligned in an end-to-end configuration, as schematically shown in FIG. 1. The rail sections 67 are generally fixedly secured together with a spline 69, or other suitable arrangement, forming a gap, barrier or boundary 71 between the adjacently spaced rail sections 67. As the vehicle 17 moves along the rail 7, the boundary 71 interferes with the refracted pulse 37 being transmitted along the rail 7. Due to such interference by the boundary 71, the signal intensities received by the sensors $S_1$, $S_2$ and $S_3$ become unstable, unpredictable or non-existent. Such interference can also be caused by mud or other obstruction of the rail 7, such as at a railroad crossing, or the like. Under such conditions, the data processor 11 will cause the displacer 65 to unsuccessfully seek the equilibrium configuration.

As a result, the system 1 includes a rail splice or boundary detector 73, such as an ultrasonic transmitter/receiver 75 (FIG. 7) whereby a pulse 77 is transmitted generally vertically, or other suitable arrangement. The pulse 77 is directed such that one of the splines 69 passing below the transmitter/receiver 75 will reflect a component 79 of the pulse 77 back to the transmitter/receiver 75. The data processor 11 is adapted to compare the combined transit time of the pulses 77 and 79 with the transit time anticipated for reflections from one of the splines 69.

Figures 7, 8:
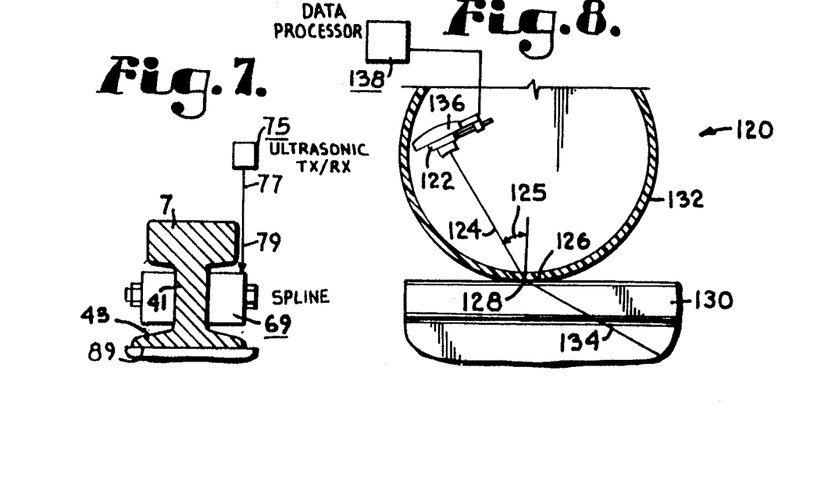
FIG. 7 is greatly enlarged transverse sectional view illustrating a boundary detector transceiver of the present invention.
FIG. 8 is a greatly enlarged fragmentary side elevational view illustrating a modified embodiment of the rail stress measuring system in which a displacement between the ultrasonic transmitter and receiver is constant and an angular orientation of the transmitter is varied.

If the observed transit time is greater or less than the anticipated transit time, the reflected pulse 77 will be ignored and the system 1 will attempt to maintain the aforesaid equilibrium configuration. If the observed transit time is approximately equal to the anticipated transit time, the data processor 11 is adapted to place the displacer 65 on standby to thereby avoid seeking for the equilibrium configuration which would be unsuccessful due to the interference caused by the boundary 71.

The data processor 11 is adapted to continue to maintain the displacer 65 in standby until the vehicle 17 has traveled a sufficient distance along the rail 7 whereby the boundary 71 corresponding to the spline 69 detected by the boundary detector 73 no longer interferes with the refracted pulse 37. For example, in one application of the present invention, the data processor 11 automatically placed the displacer on standby for a distance of approximately 39 inches along the track 7 immediately following the detection of one of the splines 69.

A displacement encoder 81 monitors the changes in longitudinal displacement between the transmitting means 3 and the receiving means 9 and communicates such information to the data processor 11 for use in determining the transit time of the refracted pulse 37 through the rail 7, as hereinafter described.

The system 1 includes a rail height detector, such as an ultrasonic transmitter/receiver 83, which transmits a longitudinal sound pulse 85 at normal incidence or perpendicular to the rail 7. As the pulse 85 encounters the rail 7, a first echo portion 86 of the pulse 85 is reflected from the top of the rail 7 such that a first echo is received by the rail height detector 83. A portion 87 of the pulse 85, which enters the rail 7, traverses the rail web 41 and a second echo portion 88 thereof is internally reflected from a bottom surface 89 of the rail base 43, which causes a second echo to be received by the rail height detector 83.

The data processor 11, in communication with the rail transmitter/receiver 83, is adapted to determine the height of the rail 7 from the time interval between receipt of the first and second echoes from the pulse 85. The rail height detector 83 repeatedly transmits one of the pulses 85, such as every 10 mm. along the rail 7.

In one application of the present invention, the transmitter 13 was spaced near one side of the test wheel 19, and the transmitter of the rail height detector 83 spaced near the opposing side of the test wheel 21, with each operating independently of the other.

The system 1 includes a rail temperature detector 91, such as an infrared temperature detector or other suitable apparatus, which is adapted to remotely measure the temperature of the rail 7. The temperature detector 91 is adapted to dynamically and continuously measure the temperature of the rail 7 as the vehicle 17 travels therealong.

The system 1 includes a site identifier 93, such as a shaft encoder system which locates the position of each of the periodic transmissions of the pulse pulses 5 along the rail 7 relative to a fixed point along the rail 7, or the like. It is foreseen that a GPS (global positioning system) may be included as an integral part of the site identifier 93.

The locations of the pulses 5 are communicated to the data processor 11, which is adapted to make a permanent record of the location and other observed and calculated data as herein described for each of the sites in a rail log 95.

The data processor 11, such as a process controller, as provided by Allen Bradley, or other suitable data processor, is adapted to communicate in real-time with the various components or peripheral devices of the system 1, including the transmitting means 3, the receiving means 9, the displacer 65, the rail splice detector 73, the displacement encoder 81, the rail height detector 83, the rail temperature detector 91, the site identifier 93, and the rail log 95. The data processor 11 includes algorithms which are designed to interrelate the inputs from these various peripheral devices to determine the velocity of propagation of the refracted pulse 37 through the rail 7.

The data processor 11 also includes algorithms to determine the longitudinal stress in the rail 7, the corresponding SFT based on the temperature of the rail 7, and the length of rail which needs to be removed or the length of plug (not shown) which needs to be inserted to correct the SFT to the PSFT, for each such site along the rail in order to avoid rail pull-aparts in Winter and rail-buckles in Summer, respectively.

The data processor 11 is adapted to automatically flag the portions of the rail 7 having critical or threshold longitudinal stress levels by conveying such corrective information to a rail marker 97, such as a remotely controlled paint sprayer, which marks the rail 7 with the appropriate corrective information. The marking may be coded to reflect that corrective information, such as preselected color coding, dots-and-dashes, or the like.

The system 1 may include a video camera 99 or the like, which is mounted near the front of the vehicle 17 such that the rails 7 of the track can be visually observed. Output from the video camera 99 may be digitized and displayed on a monitor (not shown). If desired the image from the video camera 99 may be superimposed on an image of a preferred separation of the rails 7 on the unshown monitor where variations therebetween can be visually observed by a user of the system 1. In addition, the processor 11 may be adapted to sound an alarm if the variation between the rail separation observed by the video camera 99 and the preferred separation exceeds acceptable limits.

Figure 3:
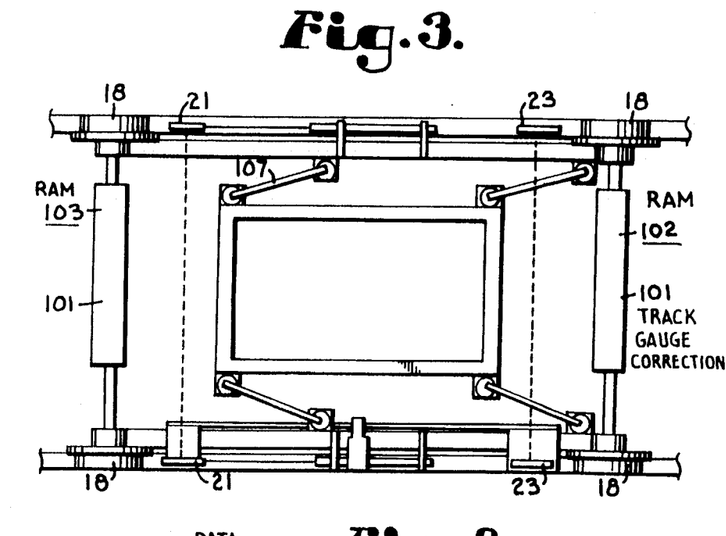
FIG. 3 is an enlarged fragmentary plan sectional view taken on line 3—3 of FIG. 2 and illustrates further details of the system vehicle, including a track gauge correction mechanism of the system.

The system 1 includes a track gauge correction mechanism 103, such as a pair of opposing, transversely oriented rams 102 and 103, as shown in FIG. 3. The rams 102 and 103 are adapted to urge each of the mated pairs of flanged wheels 18 outwardly, such as by a force of approximately 100 pounds or other suitable magnitude, in order to maintain proper alignment of the test wheels 21 and 23 with the respective rails 7.

It is foreseen that the system 1 could be combined with other types of flaw detection apparatus contained on the vehicle 17 whereby a single pass along a CR track could dynamically detect other types of rail defects simultaneously with the dynamic measurement of longitudinal stress in the rails 7.

Application

In an application of the system 1, the system 1 is calibrated by positioning the test wheels 21 and 23 on a stress-free portion of the rail 7. The transmitting means 3 is caused to tranmit a pulse 5 which is refracted into and longitudinally along the rail 7 through the rail web 41, such as along a path indicated by the solid line designated by the numeral 109 in FIG. 6.

The distance between the transmitting means 3 and the receiving means 9 is adjusted, and the focuser 51 is focused whereby a maximum signal intensity is received by the sensor $S_2$ and lesser, substantially equal signal intensities are received by the sensors $S_1$ and $S_3$. The temperature of the rail 7 is measured by the rail temperature detector 91 and the height of the rail 7 is measured by the rail height detector 83. The data processor 11 then identifies the displacement between the transmitting means 3 and the receiving means 9 as representing zero-longitudinal stress at the measured height of the rail 7 and temperature.

The systems 1 are then driven along the track with one of the systems 1 running along the top of each of the rails 7 of the track. The track gauge correction mechanism 101 maintains the systems 1 in proper alignment with the respective rails 7. Unless the rail 7 being measured by a particular one of the systems 1 is at its SFT, the triangulation of the path of the pulse 5 through the rail 7 varies from that during calibration of the system 1, such as along the dotted line designated by the numeral 111 in FIG. 6.

Figure 6:
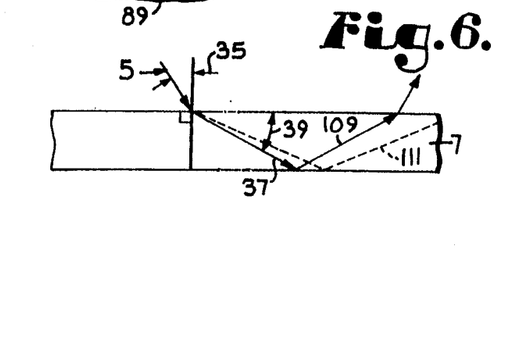
FIG. 6 is a diagrammatic view illustrating the propagation path of ultrasonic pulses employed in the rail stress measuring system of the present invention.

The change from the path 109 to the path 111 corresponds to the longitudinal stress in the rail 7, which alters the velocity of propagation of the pulse 37 through the rail 7, which alters the angle of refraction 39 of the pulse 37.

Due to the change from the path to the path 111, the relative intensities detected by the sensors $S_1$, $S_2$ and $S_3$ also changes. The digitizer 63 digitizes and communicates the relative intensities detected by the sensors $S_1$, $S_2$ and $S_3$ to the data processor 11. The data processor 11 then drives the displacer 65 such that the equilibrium configuration is reestablished, as indicated by the relative intensities detected by the sensors $S_1$, $S_2$ and $S_3$, as hereinbefore described. The change in displacement required to re-establish the equilibrium configuration is communicated to the data processor 11 by the displacement encoder 81. The magnitude of the displacement required to re-establish the equilibrium configuration is sometimes referred to herein as the stress induced linear displacement ("SILD").

For example, a 136 lb./yd. rail having a rail height of 167 mm wherein the transmitting means 3 are displaced 851.6 mm from the receiving means 9 for a velocity of propagation of 3,200 m/s, a change in shear velocity of 72 m/s to 3,272 m/s, which represents a 2.25% variation, requires a change in displacement of 186.1 mm to 1037.7 mm, which represents a 21.85% variation. In other words, the system 1 greatly amplifies the relative variations of the change in displacement relative to the shear velocity of propagation of the shear pulse 37 through the rail 7.

The rail height detector 83 provides inputs to the data processor 11 for correcting the changes in displacement between the transmitting means 3 and the receiving means 9 for changes in the height of the rail 7. Algorithms, a look-up table with values determined either empirically or theoretically, or other suitable reference, is contained in the data processor 11, which correlates the displacement required to re-establish the equilibrium configuration to the longitudinal stress in the rail 7.

The rail temperature detector 91 provides inputs to the data processor 11 whereby the SFT can be determined and compared with the PSFT for that locality. If the calculated SFT lies beyond acceptable limits from the PSFT, the data processor 11 activates the rail marker 97 which marks the rail 7 as appropriate with prescribed corrective requirements.

As the system 1 continues along the rails 7, such as at a speed of approximately 25 miles/hour, the trigger means 16 causes the transmitting means 3 to repeatedly transmit pulses through the rails 7, such as every 10 mm therealong. The site identifier 93 provides inputs to the data processor 11 whereby the transmission location of each of the pulses 5 is identified relative to a selected reference location, such as mile markers along the rails 7, or the like.

The data processor 11 causes the rail log 95 to produce a permanent, tabulated copy of the measured stress and other data corresponding to selected ones of the emitted pulses 5. The data recorded in the rail log 95 can be compared with previously acquired data in order to determine those locations in the rail 7 where deterioration is occurring, as evidenced by a change in calculated SFT where no repairs have been conducted.

Modified Embodiment

A modified rail stress measuring system in accordance with the present invention is schematically shown in FIG. 8 and is generally designated by the reference numeral 120. Many of the characteristics of the modified rail stress measuring system 120 are substantially similar to those previously described for the rail stress measuring system 1 and will not be reiterated here in detail.

The system 120 includes transmitting means 122 for transmitting a pulse 124 at a angle of incidence 125, through an interface 126 at an entry site 128 between a rail 130 and a test wheel 132 containing the transmitting means 122, and along a path 134 through the rail 130. The transmitting means 122 is slidably mounted on an arcuately shaped bracket 136 such that the transmitting means 122 pivots about the entry site 128 as the transmitting means 122 is displaced along the bracket 136.

As longitudinal stresses with the rail 130 change which tends to cause a change in the path 134 as detected by receiving means (not shown), a data processor 138 causes the transmitting means 122 to be displaced relative to the bracket 136, thereby modifying the angle of incidence 125 whereby the path 134 remains unchanged. The change in the angle of incidence 125, sometimes referred to herein as the stress induced angular displacement ("SIAD"), is used to determine the changes in longitudinal stress of the rail 130, as hereinbefore described.

For example, a 136 lb./yd. rail having a rail height of 167 mm wherein the transmitting means is positioned at an angle of 68.6° relative to the entry site 128 for a velocity of propagation of 3,200 m/s, a change in shear velocity of 72 m/s to 3,272 m/s, which represents a 2.25% variation, requires a change in the angle of incidence 125 of 3.6° to 72.2°, which represents a 5.25% variation.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for dynamically measuring the longitudinal stress in a continuous rail constructed from rail sections connected in an end-to-end configuration and having a boundary, comprising:
   (a) transmitter means transmitting an ultrasonic pulse into said rail to cause propagation through said rail in a longitudinal direction thereof;
   (b) receiver means receiving said ultrasonic pulse after propagation through said rail in a propagation path;
   (c) path measuring means connected to said receiver means and operative to measure a path variation in said path from a reference propagation path; and
   (d) processor means connected to said path measuring means and operative to evaluate a longitudinal stress in said rail from said path variation of said rail.

2. The apparatus according to claim 1, wherein:
   (a) said path variation includes a variation in an angle of refraction of said pulse as said pulse is propagated into the rail.

3. The apparatus according to claim 1, wherein:
   (a) said path variation includes a variation in an angle of incidence of said pulse as said pulse is transmitted into the rail.

4. The apparatus according to claim 1, wherein:
   (a) said transmitter means transmits a plurality of said pulses which are spaced generally uniformly along the rail.

5. The apparatus according to claim 1, wherein:
   (a) said pulse transmitted into the rail has an angle of refraction between approximately 35° and 85°.

6. The apparatus according to claim 1, wherein:
   (a) said pulse transmitted into the rail has an angle of refraction of approximately 70°.

7. The apparatus according to claim 1, including:
   (a) noise suppressing means for suppressing extraneous ultrasonic energy from said pulse received by said receiver means.

8. The apparatus according to claim 7, wherein:
   (a) said noise suppressing means includes means for impressing a code on said pulse.

9. The apparatus according to claim 7, wherein:
   (a) said receiving means include a plurality of sensors arranged in a linear array generally aligned with the rail; and
   (b) said sensors include a central sensor and non-central sensors such that the central sensor is spaced centrally to the non-central sensors.

10. The apparatus according to claim 9, including:
    (a) said noise suppressing means includes means for impressing a code on said pulse; and
    (b) a plurality of electronic filters, one for each of said sensors, said filters adapted to accept said coded pulse and to reject noise components therewith.

11. The apparatus according to claim 9, including:
    (a) comparator means adapted to compare relative amplitudes of said pulses received by said sensors.

12. The apparatus according to claim 11, including:
    (a) a displacer connected to said transmitter means and said sensors of said receiver means, said displacer adapted to adjust the displacement between said transmitter means and said sensors such that the amplitude of said pulse received by said central sensor is greater than the intensity received by any of said non-central sensors.

13. The apparatus according to claim 12, including:
    (a) a displacement encoder connected to said displacer and said processor means, said displacement encoder adapted to convey changes in said displacement between said transmitter means and said sensors to said processor means.

14. The apparatus according to claim 1, including:
    (a) a site identifier connected to said transmitter means and said processor means, said site identifier adapted to identify the site along the rail at which said pulse is transmitted into the rail.

15. The apparatus according to claim 1, including:
    (a) a rail height detector connected to said processor means, said rail height detector adapted to dynamically determine the vertical height of the rail and to convey data corresponding to said height to said processor means.

16. The apparatus according to claim 15, wherein:
(a) said rail height detector includes an ultrasonic transmitter and receiver.

17. The apparatus according to claim 1, including:
(a) a temperature detector connected to said processor means, said temperature detector adapted to dynamically and remotely measure the temperature of the rail.

18. The apparatus according to claim 17, wherein:
(a) said temperature detector utilizes infrared techniques to measure said temperature of the rail.

19. The apparatus according to claim 1, including:
(a) a rail marker connected to said processor means, said rail marker adapted to selectively mark the rail.

20. The apparatus according to claim 1, including:
(a) a boundary detector connected to said processor means, said boundary detector adapted to detect the boundary between adjacently spaced rail sections.

21. A method for dynamically measuring the longitudinal stress in a continuous rail constructed from rail sections connected in an end-to-end configuration and having a boundary, said method comprising the steps of:
(a) transmitting an ultrasonic pulse into said rail to cause propagation through said rail in a longitudinal direction thereof;
(b) receiving said ultrasonic pulse after propagation through said rail in a propagation path;
(c) measuring a path variation in said path from a reference propagation path; and
(d) evaluating a longitudinal stress in said rail from said path variation of said rail.

* * * * *